US012570343B2

(12) United States Patent
Davidson

(10) Patent No.: US 12,570,343 B2
(45) Date of Patent: Mar. 10, 2026

(54) BASE FOR A MEDICAL CART

(71) Applicant: Sunset IP Pty Ltd, Brisbane (AU)

(72) Inventor: Murray Ian Davidson, Banyo (AU)

(73) Assignee: Sunset IP Pty Ltd (AU)

( * ) Notice: Subject to any disclaimer, the term of this patent is extended or adjusted under 35 U.S.C. 154(b) by 262 days.

(21) Appl. No.: 18/023,485

(22) PCT Filed: Aug. 24, 2021

(86) PCT No.: PCT/AU2021/050949
§ 371 (c)(1),
(2) Date: Feb. 27, 2023

(87) PCT Pub. No.: WO2022/040732
PCT Pub. Date: Mar. 3, 2022

(65) Prior Publication Data
US 2024/0010258 A1      Jan. 11, 2024

(30) Foreign Application Priority Data

Aug. 25, 2020    (AU) ................................ 2020903026

(51) Int. Cl.
B62B 3/14 (2006.01)
A61B 50/13 (2016.01)
F16M 11/42 (2006.01)
(52) U.S. Cl.
CPC ............ B62B 3/1492 (2013.01); A61B 50/13 (2016.02); B62B 3/1404 (2013.01); F16M 11/42 (2013.01)
(58) Field of Classification Search
CPC . B62B 3/1492; B62B 3/1404; B62B 2301/05; A61B 50/13; A61B 2560/0437;
(Continued)

(56) References Cited

U.S. PATENT DOCUMENTS 5,690,303 A * 11/1997 Winters ................. A47B 91/00
                                                                          248/188.7
7,621,544 B2 * 11/2009 Rossini .................. F16M 11/22
                                                                          280/47.35
(Continued)

FOREIGN PATENT DOCUMENTS

CN          201504781          6/2010
CN          111012084 A   *   4/2020   ........... A47B 91/005
(Continued)

OTHER PUBLICATIONS

CN-111012084-A English Translation (Year: 2020).*
(Continued)

*Primary Examiner* — Michael T. Walsh
(74) *Attorney, Agent, or Firm* — Tumey L.L.P.

(57) ABSTRACT

A castored base for a medical cart, the base comprising: a central hub body with a plurality of legs extending radially outwardly therefrom wherein each leg comprises a socket or sleeve at an outer end of said each leg for connecting a castor to the socket or sleeve, the central hub body comprising an outer side wall extending between an upper and lower portions of the hub, the outer wall of the hub body comprising first and second leg attachment portions that are positioned at diametrically opposed locations on the outer wall of the hub body and wherein a first pair of legs is attached at the first leg attachment portion and a second pair of legs is attached at the second leg attachment portion; wherein at each of the first and second leg attachment portions, a first leg from a respective pair of legs is attached at a first attachment location on the hub body and a second leg from said respective pair is attached at a second attachment location on the hub body and wherein in-use height of the first attachment location is greater than in-use height of the second attachment location.

17 Claims, 7 Drawing Sheets

(58) Field of Classification Search
CPC ........ F16M 11/42; F16M 11/28; F16M 11/22;
F16M 2200/08; A47B 7/02; A47B
2031/006; A47B 2200/0023; A47B
2200/0076; A47B 91/005; A61G 12/001
See application file for complete search history.

(56) References Cited

U.S. PATENT DOCUMENTS

| | | | |
|---|---|---|---|
| 10,426,261 B2 * | 10/2019 | Theis | F16M 11/041 |
| 2016/0270530 A1 * | 9/2016 | Heyring | F16M 11/22 |
| 2016/0273701 A1 | 9/2016 | Heyring et al. | |
| 2017/0065074 A1 | 3/2017 | Ilse | |

FOREIGN PATENT DOCUMENTS

| | | | | | |
|---|---|---|---|---|---|
| JP | 2004187851 A | * | 7/2004 | | |
| JP | 2009-106618 | | 5/2009 | | |
| WO | WO-9959447 A1 | * | 11/1999 | ............. | A47C 3/045 |
| WO | WO-2007041725 A1 | * | 4/2007 | ............. | A47B 91/16 |

OTHER PUBLICATIONS

WO-2007041725-A1 English Translation (Year: 2007).*
JP-2004187851-A English Translation (Year: 2004).*
WO-9959447-A1 English Translation (Year: 1999).*
International Preliminary Report on Patentability for Application No. PCT/AU2021/050949 dated Dec. 8, 2022.
International Written Opinion for Application No. PCT/AU2021/050949 dated May 6, 2022.
International Written Opinion for Application No. PCT/AU2021/050949 dated Mar. 7, 2022.
International Search Report for Application No. PCT/AU2021/050949 dated Oct. 11, 2021.
International Written Opinion for Application No. PCT/AU2021/050949 dated Oct. 11, 2021.
1 European Search Report for Application No. PCT/AU2021/050949 dated Aug. 19, 2024.

* cited by examiner

BASE FOR A MEDICAL CART

TECHNICAL FIELD

The present invention relates to a castored base for a medical cart. In particular, although not exclusively, the invention relates to a castored base for a medical cart having a plurality of radiating legs, each supported by a respective castor. However, the present invention is not limited in its application to medical carts. The invention may also have application to other types of apparatus including but not limited to office chairs such as domestic chairs, and also to tables and other moveable pieces of furniture and moveable office accessories.

BACKGROUND

Any references to methods, apparatus or documents of the prior art are not to be taken as constituting any evidence or admission that they formed, or form part of the common general knowledge.

A medical cart sometimes has wheels to enable it to be moved easily from one room to another or moved within a room, so that a procedure can be performed or another use made of the medical cart. Typical medical carts also hold equipment, such as electronic equipment, that relates to the procedure or other use.

One of the problems associated with currently known medical carts relates to ease of storage during transport and during periods of non-use. Medical carts can often be used for mounting heavy and expensive medical equipment which may need to be stored temporarily during periods of non-use or maintenance. Medical carts are typically provided with a castored base which provides high levels of stability during use. However, the currently known castored base designs do not easily allow multiple carts to be stacked or nested in a compact and efficient manner. Whilst, nesting is possible to a limited extent in some prior art carts, there remains a need for an improved medical cart that addresses some of the shortcomings of the prior art.

SUMMARY OF INVENTION

In an aspect, the invention provides a base for a medical cart, the base comprising:

a central hub body with a plurality of legs extending radially outwardly therefrom wherein each leg comprises a socket or sleeve at an outer end of said each leg for connecting a castor to the socket or sleeve, the central hub body comprising an outer side wall extending between an upper and lower portions of the hub, the outer side wall of the hub body comprising first and second leg attachment portions that are positioned at diametrically opposed locations on the outer side wall of the hub body and wherein a first pair of legs is attached at the first leg attachment portion and a second pair of legs is attached at the second leg attachment portion;

wherein at each of the first and second leg attachment portions, a first leg from a respective pair of legs is attached at a first attachment location on the hub body and a second leg from said respective pair is attached at a second attachment location on the hub body and wherein in-use height of the first attachment location is greater than in-use height of the second attachment location.

In an embodiment, each leg comprises a socket or sleeve at an outer end of said each leg with a castor connected to the socket or sleeve In an embodiment, the first leg at the first attachment portion extends in an opposite direction relative to the first leg at the second attachment portion.

Preferably, the first leg at the first attachment portion is substantially parallel to the first leg at the second attachment portion.

In an embodiment, the second leg at the first attachment portion extends in an opposite direction relative to the second leg at the second attachment portion.

In an embodiment, the second leg at the first attachment portion is substantially parallel to the second leg at the second attachment portion.

In an embodiment, length of the socket or sleeve located at the end of the first leg attached at the first and second attachment locations is greater than length of the socket or sleeve located at the end of the second leg attached at the first and second attachment locations In an embodiment, the central hub body comprises a rectangular cross section with four mutually perpendicular side wall portions forming said side wall of the hub body.

In an embodiment, the first leg attachment portion with the first pair of legs is located on a first of said four side wall portions and the second leg attachment portion with the second pair of legs being located on a second of said four side wall portions and wherein the first and second wall portions are substantially parallel to each other and separated by third and fourth of said side wall portions.

In an embodiment, the first leg and second leg in each pair of legs lie in mutually intersecting planes in at least one operable configuration.

In an embodiment, the hub body comprises a hollow internal cavity for receiving a support column for supporting medical equipment.

In an embodiment, the radially extending legs extend in a substantially horizontal orientation.

In an embodiment, the legs incorporate a small downward gradient as they extend radially outward.

In an embodiment, the legs are of plate-like construction.

In an embodiment, each leg incorporates a longitudinally extending strengthening web disposed on its underside.

In an embodiment, each socket or sleeve is an integrally formed part of the respective leg.

In an embodiment, in a nested configuration, the first leg from the first or second attachment portions in a first said castored base is adapted to be accommodated directly above the second leg from the first or second attachment portions in a second of said castored base thereby allowing the first and second legs of the first and second castored bases to nest in the nested configuration.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
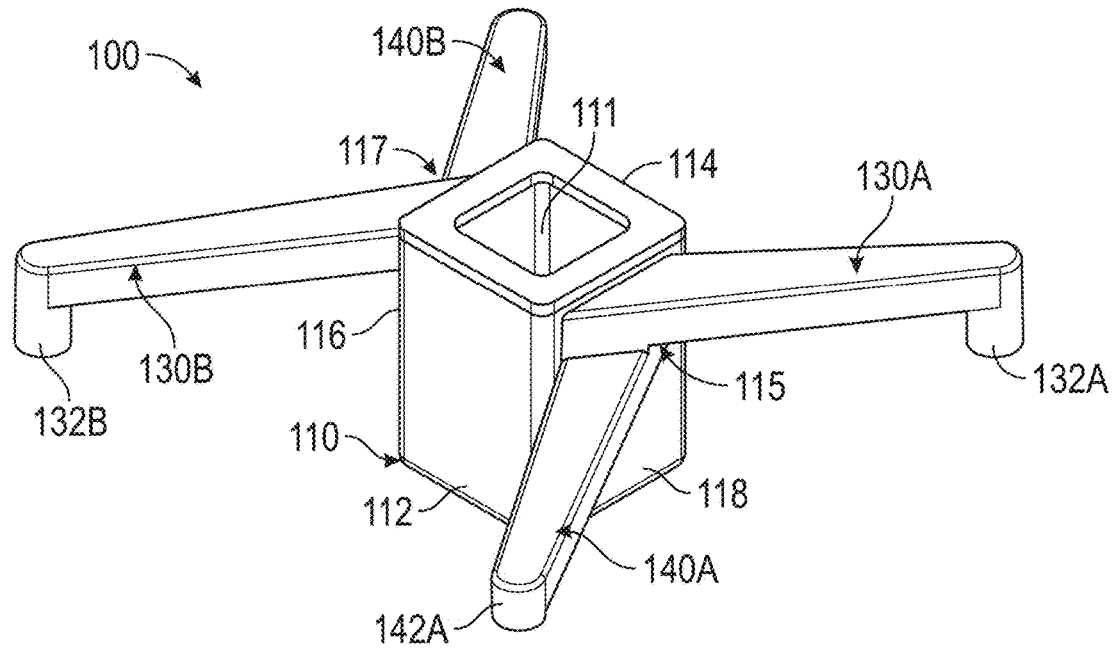
FIG. 1 is a top perspective view of a base 100 for a medical cart in accordance with a first embodiment of the present invention.
Figure 2:
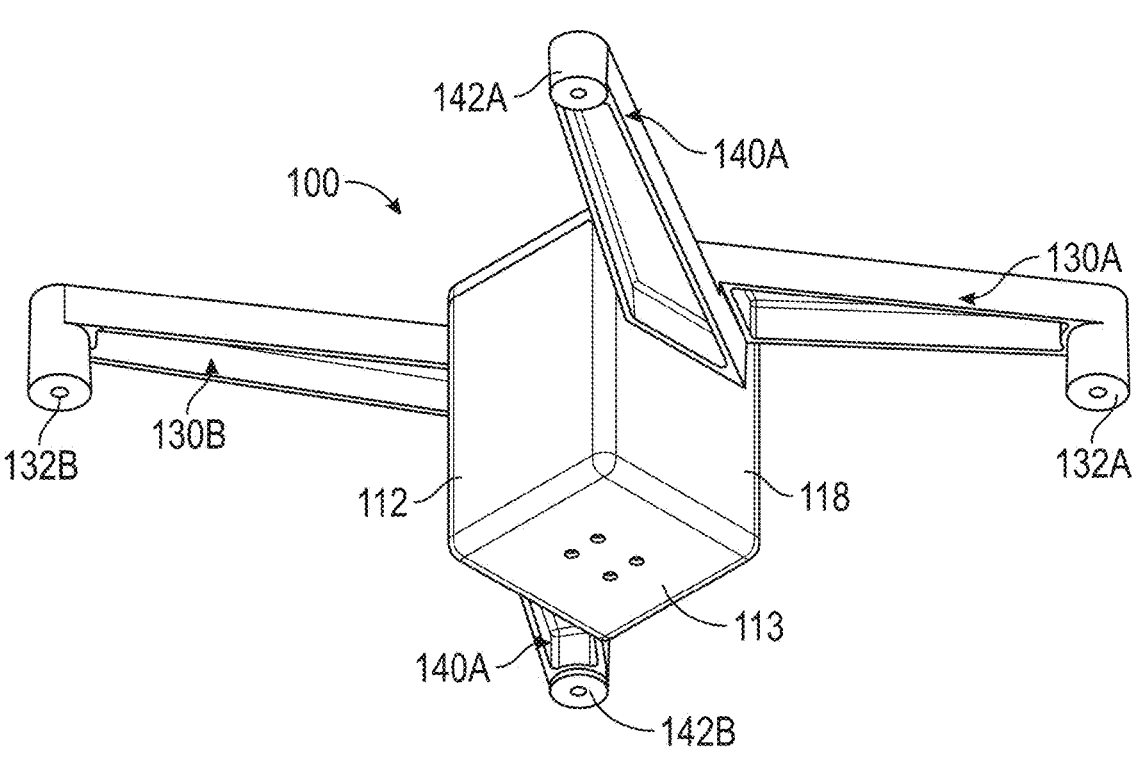
FIG. 2 is a bottom perspective view of the base 100.
Figure 3:
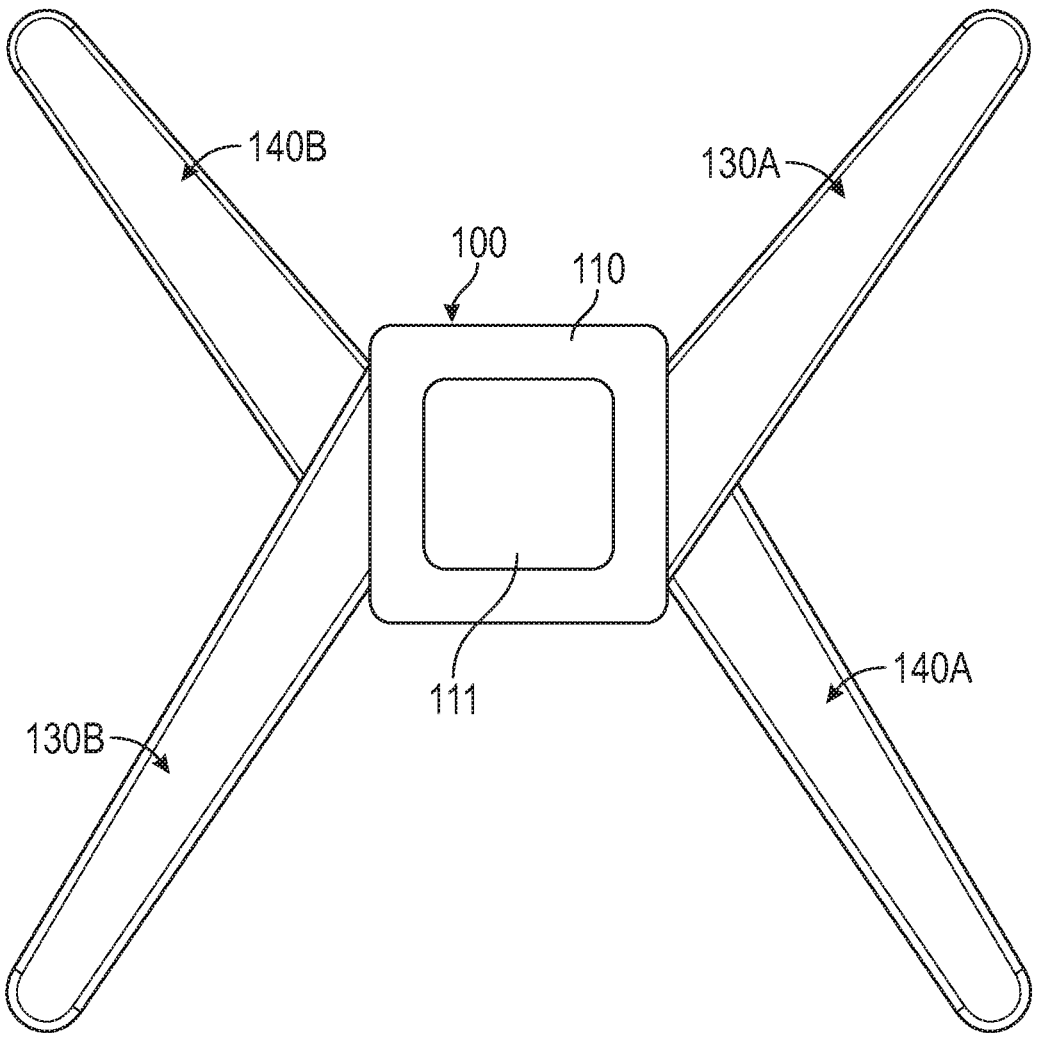
FIG. 3 is an underside view of the base 100.
Figure 4:
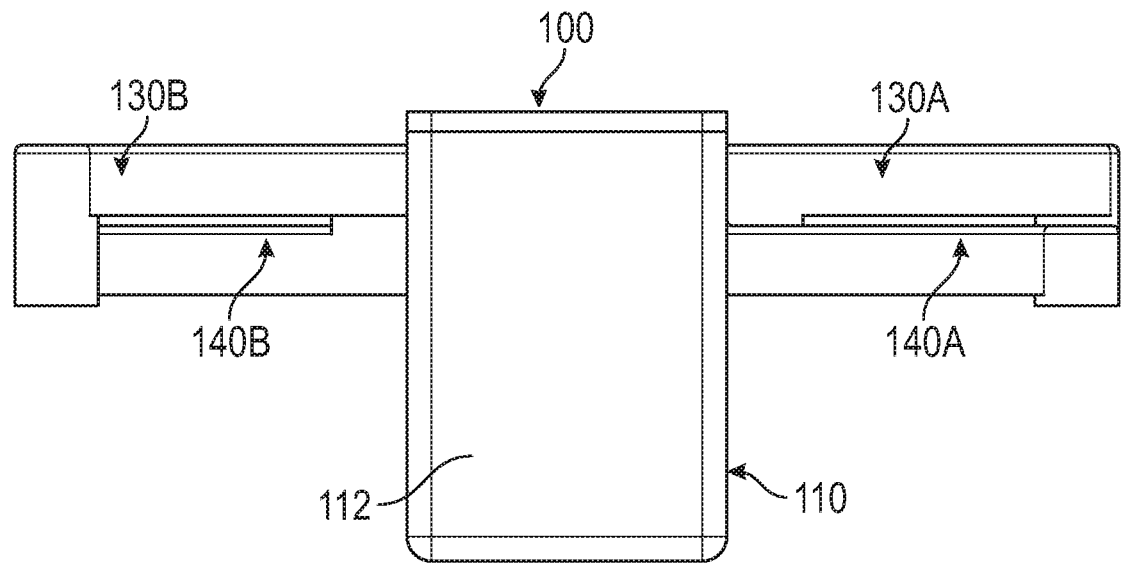
FIG. 4 is a first side view of the base 100.
Figure 5:
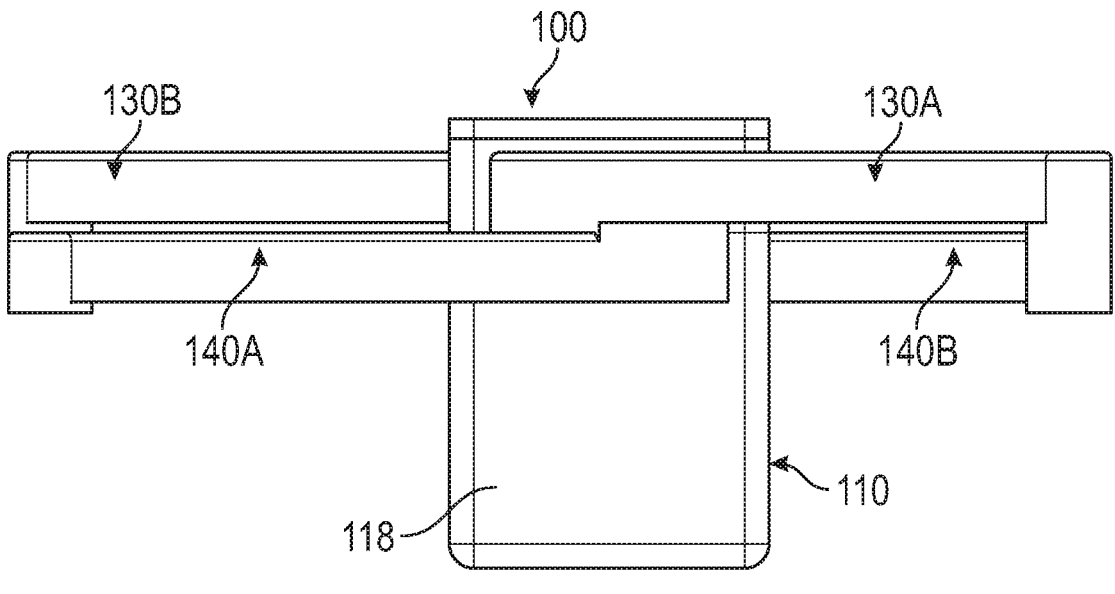
FIG. 5 is a second side view of the base 100.
Figure 6:
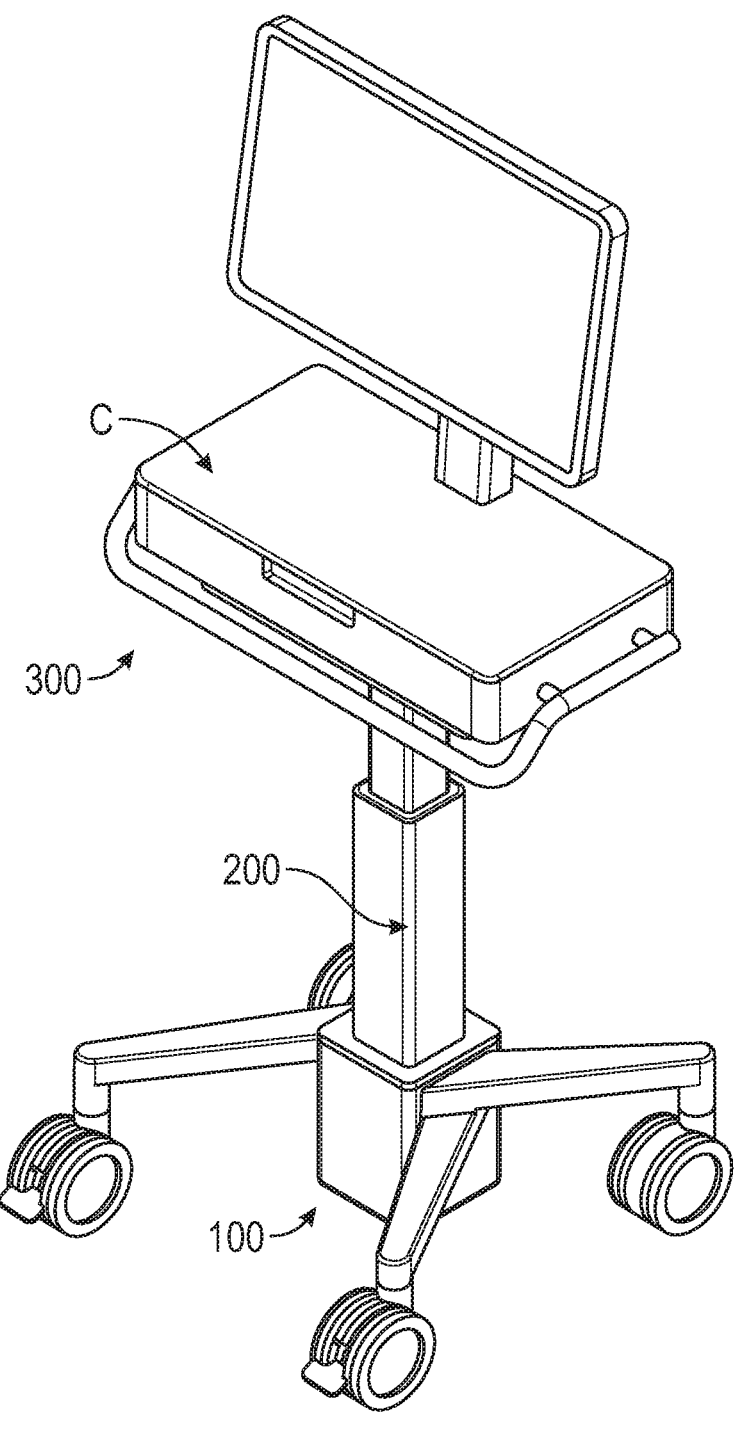
FIG. 6 is a perspective view of a medical cart 300 utilising the base 100.
Figure 7:
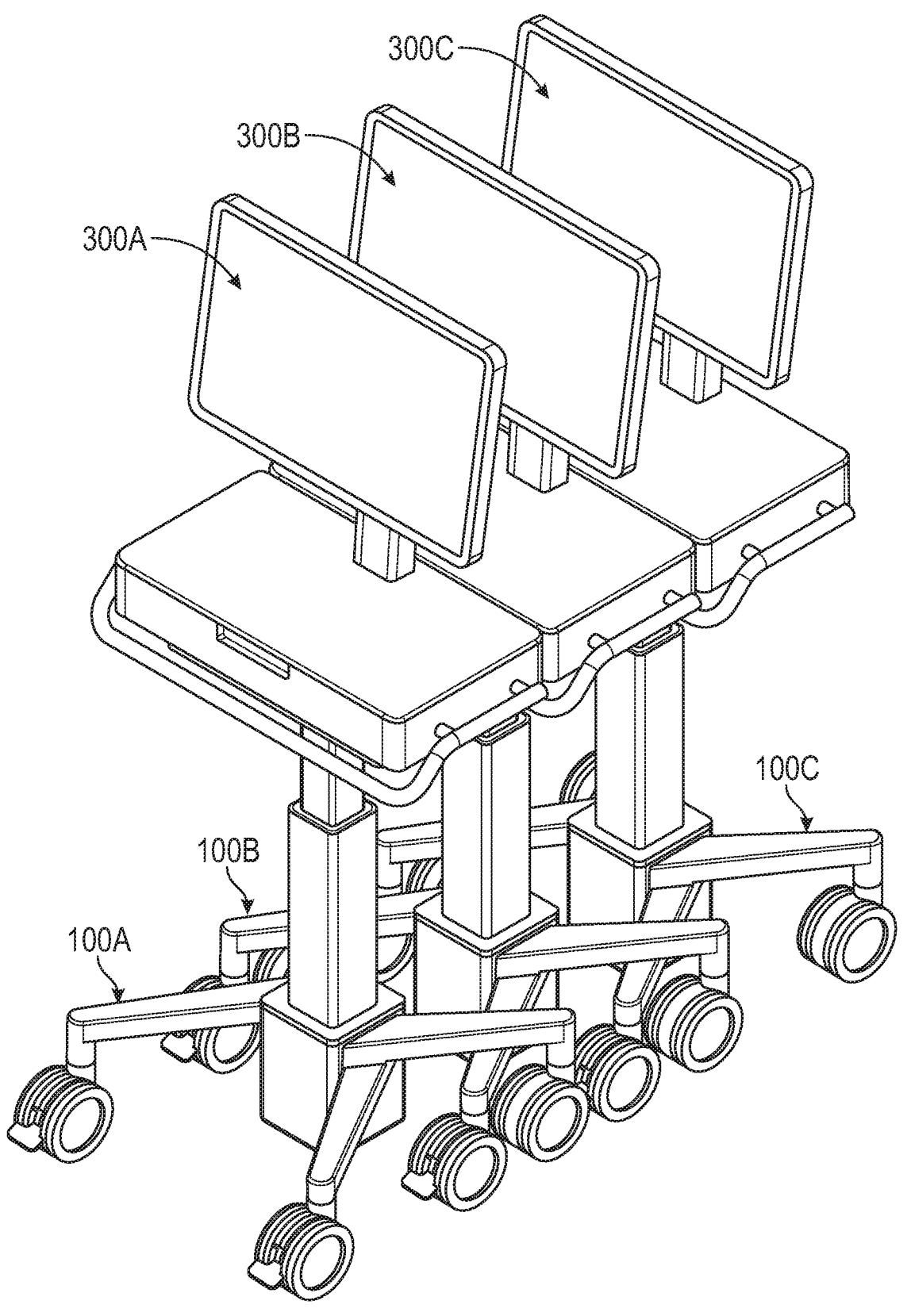
FIG. 7 is a perspective view of three medical carts 300A, 300B, 300C each utilising the base 100 (denoted by 100A, 100B and 100C) shown in a nested configuration.
Figure 8:
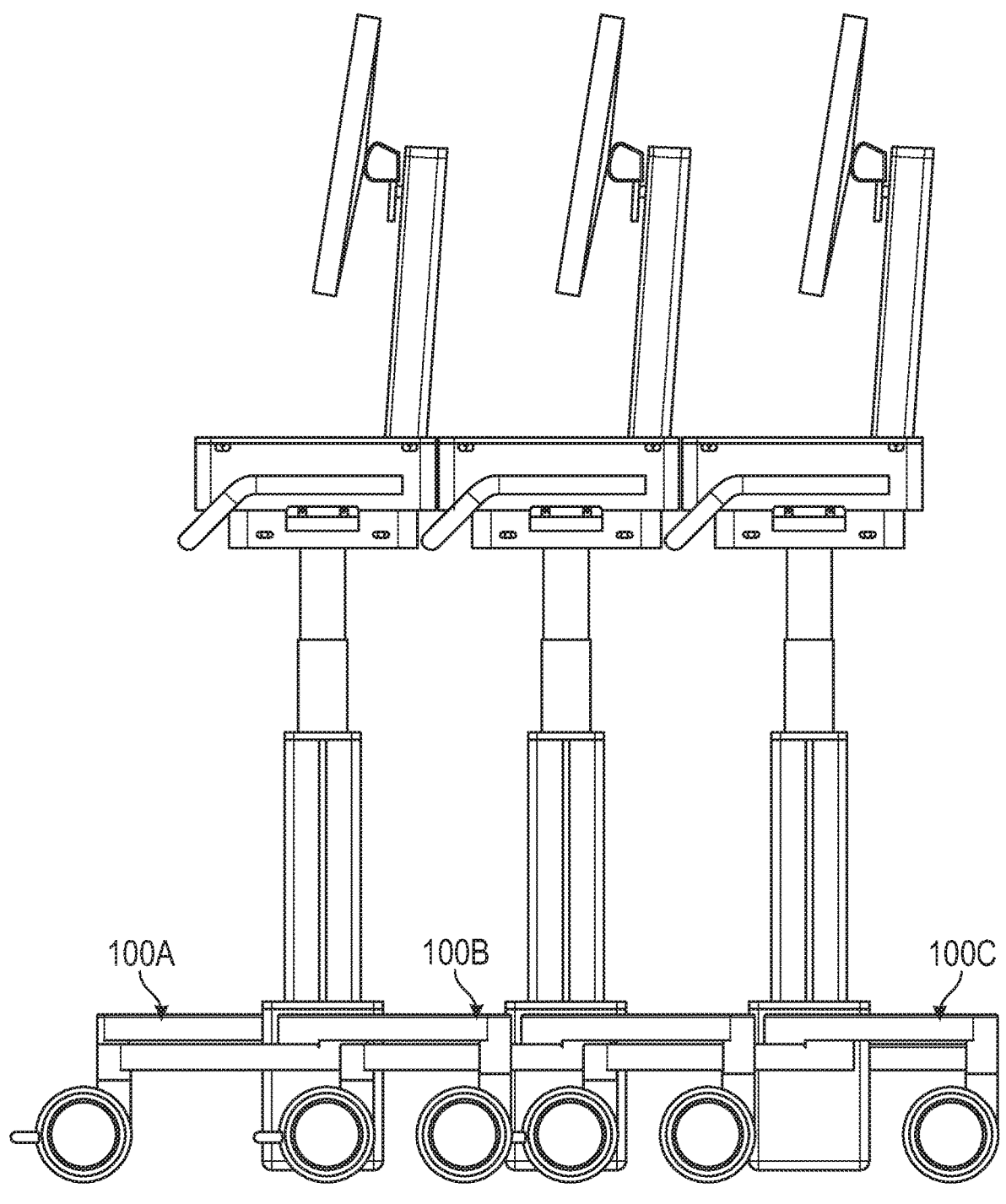
FIG. 8 is a side view of three medical carts 300A, 300B, 300C each utilising the base 100 (denoted by 100A, 100B and 100C) shown in a nested configuration.
Figure 9:
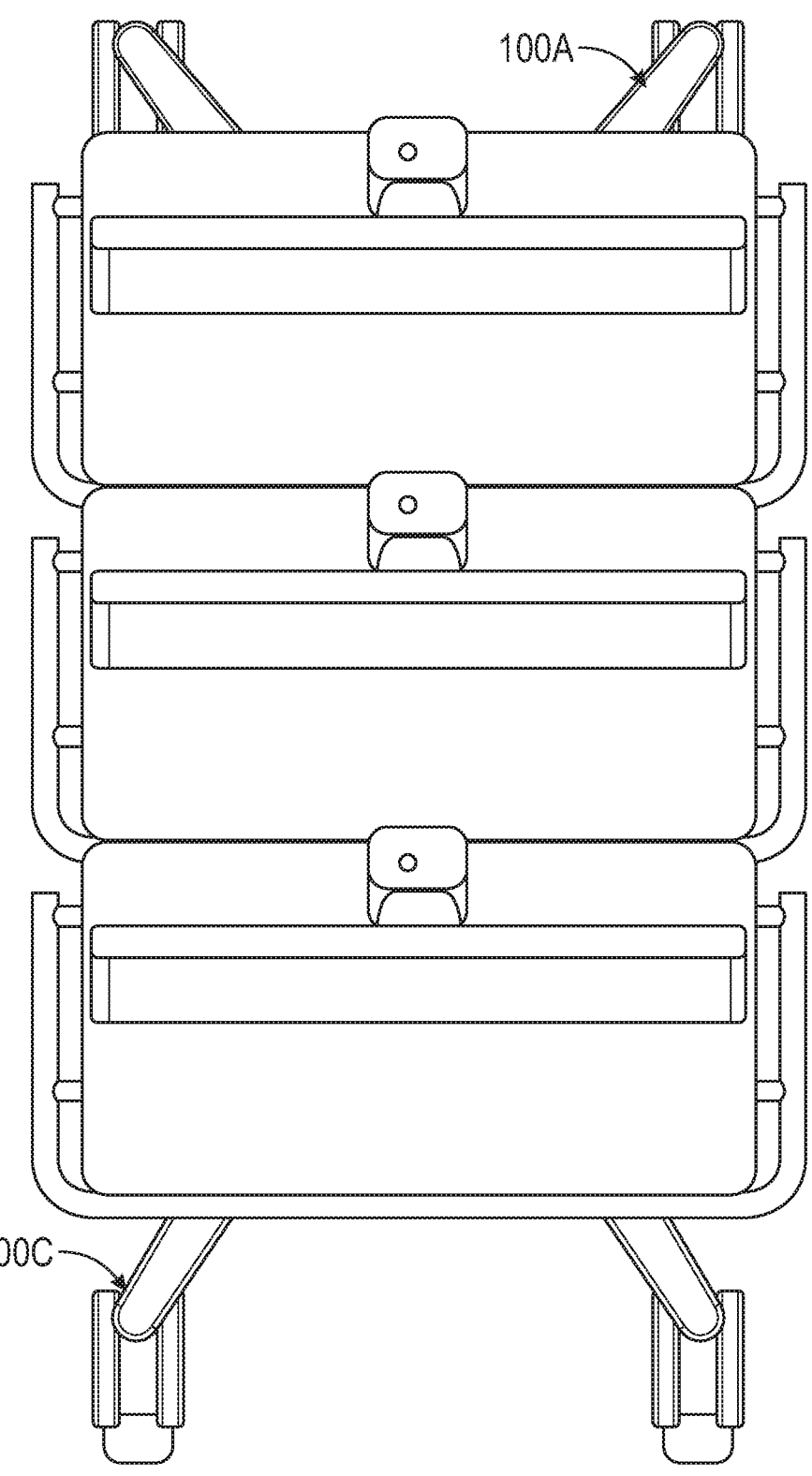
FIG. 9 is a top view of three medical carts 300A, 300B, 300C each utilising the base 100 (denoted by 100A, 100B and 100C) shown in a nested configuration.

FIGS. 1 to 9 illustrate a castored base 100 for supporting a medical cart C (shown only in FIGS. 6 to 9). FIGS. 1 to 5 illustrate isolated views of the base 100 that will be discussed in further detail. FIG. 6 illustrates medical cart 300 having a support post 200 supported on the castored base 100 wherein the support post 200 is configured to support a medical equipment receiving frame C. It is to be understood that the base 100 may be used on conjunction with a number of alternative support post structures or equipment receiving frames without departing from the spirit and scope of the invention.

The base 100 comprises a central hub body 110 with two pairs of legs, each pair of legs comprising legs 130 and 140 (wherein suffix A denotes a first pair of legs and suffix B denotes a second pair of legs) with each leg 130 and 140 further comprising a respective socket 132 and 142 at an outer end of said each leg (130 and 140) with a castor (not shown in FIGS. 1 to 5) connected to the sockets 132 and 142.

The central hub body 110 comprises a hollow cavity 111 for receiving the supporting post 200 with an outer wall of the hub body 110 comprising four side wall portions 112, 114, 116 and 118 that are mutually perpendicular to form a substantially square shaped cross section. Two of said opposed and parallel side wall portions 116 and 118 include first and second leg attachment portions 115 and 116. At the first leg attachment portion 115, first and second legs 130A and 140A (the first pair of legs) are attached to the hub body 110. Similarly, at the second leg attachment portion 117, first and second legs 130B and 140B (the second pair of legs) are attached to the hub body 110. As is evident particularly from FIGS. 1 to 3, the first and second attachment locations 115 and 117 are positioned at diametrically opposite locations.

1. At each of the first and second leg attachment portions 115 and 117, the first leg 130 (either 130A at attachment portion 115 or 130B at attachment portion 117) from a respective pair of legs is attached at a first attachment location (L1) on the hub body 110 and a second leg 140 (either 140A at attachment portion 115 or 140B at attachment portion 117) from said respective pair is attached at a second attachment location L2 on the hub body 110. The in-use height H1 for the first attachment location L1 on the outer wall of the hub body 110 is greater than in-use height H2 of the second attachment location L2. As shown particularly clearly in FIGS. 1 to 3, the first leg 130A at the first attachment portion 115 extends in an opposite direction relative to the first leg 130B at the second attachment portion 117 and the first legs 130A and 130B are parallel to each other and extend in opposite directions. Similarly, the second leg

140A at the first attachment portion 115 extends in an opposite direction relative to the second 140B at the second attachment portion 117 and the second legs 140A and 140B are parallel to each other and extend in opposite directions.

The difference of height for the attachment locations L1 and L2 requires the sockets 132 and 142 to be at separate heights. Length of the socket 132 located at the end of the first leg 130 attached at the first and second attachment locations L1 and L2 is greater than length of the socket located at the end of the second leg 140 attached at the first and second attachment locations L1 and L2. As a result, even though the legs are attached at different heights, the height difference is compensated by the difference in the length of the sockets 132 and 142 and allows the base 100 to be positioned in a stable manner on an underlying surface when castor wheels are attached to the sockets 132 and 142.

The first and second legs 130 and 140 in each pair of legs lie in mutually intersecting planes in at least one operable configuration. In the preferred embodiment, the first and second legs 130 and 140 intersect at 90 degrees in a substantially horizontal orientation relative to the longitudinal axis of the support post 200 as shown in the accompanying figures. Each of the legs 130 and 140 may incorporate a small downward gradient as they extend radially outward. The legs 130 and 140 have a plate like construction and each leg incorporates a longitudinally extending strengthening web disposed on its underside.

Turning to FIGS. 6 to 9, the novel configuration of the legs 130 and 140 at each of the attachment portions 115 and 117 at differing attachment locations L1 and L2 (with a height difference) provides an asymmetric configuration which allows a plurality of the base units 100 (denoted by 100A, 100B and 100C) to be conveniently nested during periods of non-use. The first leg 130 from the first or second attachment portions 115 or 117 in a first said castored base is adapted to be accommodated directly above the second leg 140 from the first or second attachment portions 115 and 117 in a second of said castored base 100 thereby allowing the first and second legs 130 and 140 of the first and second castored bases to nested relative to each other.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

The invention claimed is:

1. A castored base for a medical cart, the base comprising: a central hub body with a plurality of legs extending radially outwardly therefrom wherein each leg comprises a socket or sleeve at an outer end of said each leg for connecting a castor to the socket or sleeve, the central hub body comprising an outer side wall extending between upper and lower portions of the hub, the outer side wall of the hub body comprising a first leg attachment portion and a second leg attachment portions that are positioned at diametrically opposed locations on the outer side wall of the hub body and wherein a first pair of legs is attached at the first leg attachment portion and a second pair of legs is attached at the second leg attachment portion;

wherein at each of the first and second leg attachment portions, a first leg from a respective pair of legs is attached at a first attachment location on the hub body and a second leg from said respective pair is attached at a second attachment location on the hub body and wherein in-use height of the first attachment location is greater than in-use height of the second attachment location.

2. A castored base in accordance with claim 1 wherein the first leg at the first attachment portion extends in an opposite direction relative to the first leg at the second attachment portion.

3. A castored base in accordance with claim 2 wherein the first leg at the first attachment portion is substantially parallel to the first leg at the second attachment portion.

4. A castored base in accordance with claim 1 wherein the second leg at the first attachment portion extends in an opposite direction relative to the second leg at the second attachment portion.

5. A castored base in accordance with claim 4 wherein the second leg at the first attachment portion is substantially parallel to the second leg at the second attachment portion.

6. A castored base in accordance with claim 1 wherein length of the socket or sleeve located at the outer end of the first leg attached at the first and second attachment locations is greater than length of the socket or sleeve located at the outer end of the second leg attached at the first and second attachment locations.

7. A castored base in accordance with claim 1 wherein the central hub body comprises a rectangular cross section with four mutually perpendicular side wall portions forming said side wall of the hub body.

8. A castored base in accordance with claim 7 wherein the first leg attachment portion with the first pair of legs is located on a first of said four side wall portions and the second leg attachment portion with the second pair of legs being located on a second of said four side wall portions and wherein the first and second wall portions are substantially parallel to each other and separated by third and fourth of said side wall portions.

9. A castored base in accordance with claim 1 wherein the first leg and second leg in each pair of legs lie in mutually intersecting planes in at least one operable configuration.

10. A castored base in accordance with claim 1 wherein the hub body comprises a hollow internal cavity for receiving a support column for supporting medical equipment.

11. A castored base in accordance with claim 1 wherein the radially extending legs extend in a substantially horizontal orientation relative to a vertical axis of the central hub.

12. A castored base in accordance with claim 1 wherein the legs incorporate a small downward gradient as they extend radially outward from the central hub.

13. A castored base in accordance with claim 1 wherein the legs are of plate-like construction.

14. A castored base in accordance with claim 1 wherein each leg incorporates a longitudinally extending strengthening web disposed on its underside.

15. A castored base in accordance with claim 1 wherein each socket or sleeve is an integrally formed part of the respective leg.

16. A castored base in accordance with claim 1 wherein in a nested configuration, the first leg from the first or second attachment portions in a first said castored base is adapted to be accommodated directly above the second leg from the first or second attachment portions in a second of said castored base thereby allowing the first and second legs of the first and second castored bases to nest in the nested configuration.

17. A castored base in accordance with claim 1 wherein each leg comprises a socket or sleeve at an outer end of said each leg with a castor connected to the socket or sleeve.

* * * * *